United States Patent [19]

Wagner

[11] Patent Number: 5,001,054
[45] Date of Patent: Mar. 19, 1991

[54] METHOD FOR MONITORING GLUCOSE

[75] Inventor: Daniel B. Wagner, Raleigh, N.C.

[73] Assignee: Becton, Dickinson and Company, Franklin Lakes, N.J.

[21] Appl. No.: 560,913

[22] Filed: Jul. 31, 1990

Related U.S. Application Data

[62] Division of Ser. No. 878,560, Jun. 26, 1986.

[51] Int. Cl.$^5$ .............................................. C12M 1/34
[52] U.S. Cl. ...................................... 435/14; 128/637; 128/665; 422/82.06; 422/82.07; 422/82.08; 424/9; 435/25; 436/95; 436/136; 436/138; 436/800; 436/805; 436/904
[58] Field of Search ................... 422/58, 82.06, 82.07, 422/82.08; 356/39, 445; 128/637, 665; 435/14, 25, 288, 310; 436/95, 136, 138, 800, 805, 904; 424/9

[56] References Cited

U.S. PATENT DOCUMENTS

| | | |
|---|---|---|
| 4,306,877 | 12/1981 | Lübbers ............................ 422/68.01 |
| 4,317,879 | 3/1982 | Busby et al. . |
| 4,330,299 | 5/1982 | Cerami . |
| 4,390,621 | 6/1983 | Bauer . |
| 4,392,433 | 7/1983 | Nakamura et al. . |
| 4,399,099 | 8/1983 | Buckles . |
| 4,431,004 | 2/1984 | Bessman et al. . |
| 4,436,094 | 3/1984 | Cerami . |
| 4,452,887 | 6/1984 | Kitajima et al. . |
| 4,460,684 | 7/1984 | Bauer . |
| 4,476,870 | 10/1984 | Peterson et al. . |
| 4,548,907 | 10/1985 | Seitz et al. ......................... 422/68.01 |
| 4,682,895 | 7/1987 | Costello ................................ 422/58 |
| 4,737,343 | 4/1988 | Hirschfeld ........................ 422/68.01 |

OTHER PUBLICATIONS

Biomedical Tech., "New Blood Glucose Monitoring System From Boehringer Mannheim," vol. 12, No. 11, p. 123, Nov. 1, 1985.

*Primary Examiner*—Robert J. Warden
*Assistant Examiner*—Timothy M. McMahon
*Attorney, Agent, or Firm*—Richard E. Brown

[57] ABSTRACT

A method for monitoring the glucose level in a body fluid uses an apparatus which includes a conjugate of glucose oxidase and a fluorescent dye coated onto an optical fiber in contact with the body fluid, a source of excitation light and a fluorescence emission detector. Glucose is oxidized by oxygen in the body fluid causing a decrease in oxygen concentration at the enzyme. The fluorescent dye is sensitive to oxygen quenching so that, when the oxygen concentration decreases, fluorescence emission increases in direct proportion to the glucose concentration in the fluid.

9 Claims, 4 Drawing Sheets

METHOD FOR MONITORING GLUCOSE

This is a division of application Ser. No. 06/878,560, filed June 26, 1986.

BACKGROUND OF THE INVENTION

1. Field of the Invention

This invention relates to monitoring glucose levels, and more particularly relates to an implantable glucose sensor and a method for using same for detection or quantitation of an elevated glucose level in a body fluid.

2. Background Description

Over five million Americans have diagnosed diabetes and another five million are estimated to have undiagnosed diabetes. Diabetes is a chronic metabolic disorder manifested by degenerative disease of the blood vessels, kidneys, retina and nervous system and is characterized by the body's abnormal metabolism of carbohydrates, proteins and fats. Carbohydrates are normally digested to glucose in the gut, the glucose being absorbed into the circulatory system and carried to most cells of the body where, it is utilized as the principal source of nutrition. In one form of diabetes, the glucose cannot enter the liver, muscle and fat cells in normal amounts for storage or energy use and as a consequence builds up in the blood and urine. Abnormally high blood glucose levels may lead to the accumulation of toxic ketone metabolites often leading to coma and death.

Glucose is normally present in the blood stream at a level of about 0.8 to 1.0 mg/ml and is maintained within this narrow range by a continuous moment to moment sensing and correction of the glucose concentration by hormones released from the pancreas. If glucose concentration in the blood stream rises above the normal range, insulin is released and causes metabolism of glucose which lowers the concentration. If the glucose concentration falls below the normal range, glucogen is released to raise it to normal. The pathological condition of diabetes is primarily due to a long term hyperglycemia resulting from reduced insulin production or release.

Many diabetics control their disease merely by diet and weight control. Others require drug treatment, generally insulin or an oral hypoglycemic agent, to control blood glucose levels. Oral administration of insulin is not practical because it is destroyed by proteolytic enzymes in the gastro-intestinal tract. Injected insulin provides only partial control of the degenerative effects of diabetes, apparently because periodic injections do not closely correspond to changing metabolic requirements consequent to fluctuating blood glucose levels. For this reason, a variety of methods have been proposed for rapid and accurate assessment of blood glucose levels.

Glucose measurement systems known in the art are generally based on the oxidation of glucose by oxygen in the presence of glucose oxidase. U.S. Pat. Nos. 4,452,887 to Kitajina et al., and 4,390,621 and 4,460,684 to Bauer exemplify a chromogenic system in which hydrogen peroxide formed during the oxidation oxidizes a substrate in the presence of peroxidase to produce a color which is measured.

Conversion of the chemical energy of the oxidation reaction to electrical energy, which is measured at electrodes, is the subject of U.S. Pat. Nos. 4,392,933 to Nakamura et al., 4,436,094 to Cerami, 4,431,004 to Bessman et al. and 4,317,817 to Busby.

Cerami, in U.S. Pat. No. 4,330,299, discloses an indicator element, such as a dye, as part of a complex containing a carbohydrate or a lectin. The indicator remains undetected until released from the complex by glucose in direct proportion to the glucose concentration.

Boehringer Mannheim Diagnostics (Indianapolis, IN) recently marketed an in vitro enzyme-based blood glucose monitoring system, (Accu-Chek TM Chemstrip bG TM), which may be read colorimetrically or photoelectronically.

Fiber optic probes for determination of oxygen pressure in a body fluid have been described. Peterson et al., in U.S. Pat. No. 4,476,870, disclose an implantable device for measurement of partial oxygen pressure in a blood stream based on oxygen quenching of fluorescence.

U.S. Pat. No. 4,399,099 to Buckles discloses a dual fiber optic device useful in a method for measuring glucose concentration. Oxygen permeable sheaths containing an oxygen quenchable fluorescent dye surround optical fibers, one of the sheaths containing glucose oxidase. The enzyme oxidizes glucose and thereby lowers oxygen concentration which is detected by reduced quenching of the fluorescence emission from the dye.

Prior art methods and devices disclosed to date for glucose measurement all suffer from deficiencies such as insufficient accuracy, speed or use of methodology or equipment which is impractical for an implantable device. There remains a definite need for a simple and accurate method for glucose monitoring using a small, light and compact apparatus. It is toward fulfillment of this need that the present invention is directed.

SUMMARY OF THE INVENTION

One aspect of the present invention is a method to detect, either in vivo or in vitro, a glucose level in a body fluid which differs from a reference level. A fluorescent dye, the fluorescence emission of which is sensitive to oxygen quenching so that the emission is maximum in the absence of oxygen, is conjugated to active glucose oxidase. The dye conjugated to active glucose oxidase is hereinafter called the test dye. The dye-enzyme conjugate is immobilized in contact with a body fluid, and glucose in the fluid is oxidized at the active enzyme with consumption of oxygen. The oxygen concentration at the dye is thereby reduced in inverse proportion to the extent of oxidation and therefore also to the glucose concentration. Application of excitation light to the dye causes fluorescence emission, which is measured. The magnitude of the emission is inversely proportional to oxygen concentration at the dye and therefore directly proportional to glucose concentration in the fluid.

The dye may also be conjugated to inactivated glucose oxidase, hereinafter called the control dye. This conjugate is also immobilized in contact with the body fluid. Glucose in the fluid is not oxidized by the inactive enzyme and the oxygen concentration at the control dye therefore remains unchanged. Quenching therefore does not occur, and the magnitude of fluorescence emission from the control dye remains constant, irrespective of changing glucose concentration, and provides a base line control for comparison with the magnitude of emission from the test dye which does fluctuate in proportion to glucose concentration. If emission from the test dye is greater than that from the control dye, an elevated glucose concentration in the fluid is indicated.

The method of the invention may also be used to quantitate the glucose concentration in the body fluid. In this embodiment of the invention, the magnitude of the fluorescence emission from the test dye may be compared with the magnitude of emission measured when the fluid contains a predetermined quantity of glucose. Emission from a plurality of fluids containing predetermined quantities of glucose may be measured to prepare a standard curve which relates glucose concentration in the fluid to the magnitude of fluorescence emission.

Another aspect of the invention is a glucose-monitoring apparatus. The two conjugates having active and inactive enzymes, described above, are coated onto the surfaces of separate optical fibers adapted for insertion into the fluid to be tested. The apparatus includes a suitable source of excitation light and a suitable fluorescence emission detector. The excitation light passes through the fibers, excites the dyes and induces fluorescence emission which passes back through the fibers where it is detected by the detector.

The preferred apparatus has four fibers, two for passage of excitation light from the light source to the dye-conjugates and two for passage of fluorescence emission from the dye conjugates to the detector. The most preferred apparatus has two pairs of concentric fibers and uses a light emitting diode (LED) as light source and a photocell as detector. One pair of fibers is coated with active enzyme-dye conjugate and is further coated with a glucose permeable membrane. The dye in this conjugate serves as the test dye. The other pair is also coated with active enzyme-dye conjugate, but is further coated with an oxygen permeable membrane which precludes passage of glucose so that the enzyme is effectively rendered inactive and its dye serves as the control dye. One fiber in each pair introduces excitation light to the conjugate and the other fiber in each pair conducts fluorescence emission from the conjugate to the detector.

Thus, in accordance with the invention, an elevated glucose level in a body fluid may be detected or quantitated, in vivo or in vitro, by a method using a glucose monitoring apparatus. The apparatus employs glucose oxidase covalently conjugated to a fluorescent dye whereby the dye and the enzyme are in close proximity so that the local oxygen concentration at the site of the enzyme reaction can be determined with exceptional accuracy. The apparatus includes an optical fiber which may be very thin and flexible thereby providing advantages for comfort and safety when inserted into the body fluid through the skin. The LED and photocell of the preferred apparatus are small and light and may easily be assembled into a simple and inexpensive unit to be either implanted or worn externally on the surface of the body, and may, if desired, be used in conjunction with any insulin delivery system. Because of these and other features, the apparatus of the invention may easily and safely be used on an outpatient basis.

DETAILED DESCRIPTION OF THE INVENTION

Figures 1, 2:
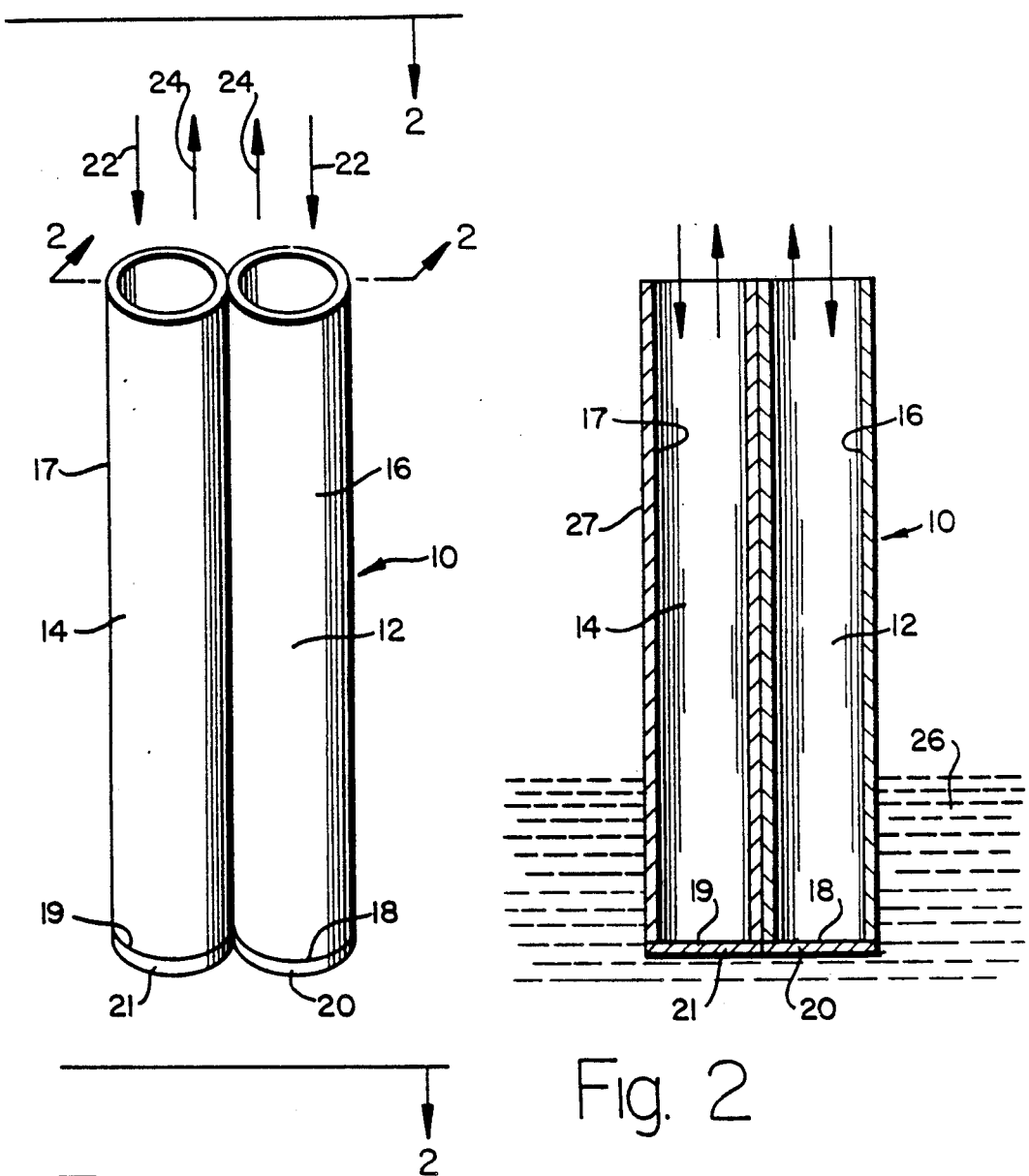
FIG. 1 is a perspective view of an apparatus of the invention using two optical fibers.
FIG. 2 is a vertical sectional view of the apparatus of FIG. 1 taken along line 2—2 thereof.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The method of the present invention for continuous monitoring of glucose in a body fluid is based on the well-known oxidative conversion of glucose to gluconic acid catalyzed by glucose oxidase. When glucose is oxidized, the consumption of oxygen causes a decrease in the local oxygen concentration at the active site of the enzyme. This decrease is proportional to glucose concentration and may be detected by fluorescence emission from a dye conjugated to the enzyme. Glucose oxidase is a well-known and well-characterized enzyme and is commercially available, for example, from Sigma Chemical Co., St. Louis, Missouri.

The dye to be conjugated to the enzyme may be any fluorescent dye sensitive to quenching of its fluorescence emission by oxygen. Such a dye fluoresces with maximum intensity in the absence of oxygen, and the intensity of its fluorescence emission is decreased in inverse proportion to the oxygen concentration in the immediate vicinity of the dye. Such dyes preferably are hydrophobic fluorescent dyes having strong absorbance in the visible part of the spectrum. Exemplary of, but not limited to, such dyes are those listed in Peterson et al. (op. cit.), preferably perylene dibutyrate, most preferably fluoranthrene.

Conjugation of the dye to the enzyme may be carried out by any conventional procedure as, for example, by covalently coupling active functional groups on the dye and enzyme. The functional groups may be bonded directly, as in amide bond formation between amino and carboxyl groups, or they may be coupled through linking groups which couple, for example, amino, hydroxyl or sulfhydryl groups on one component to a carboxyl group on the other component. Suitable linking groups may be, for example, but not limited to, a methylene chain of from one to six carbon atoms. If desired, the technique of affinity labeling may be used to conjugate the dye near the active site of the enzyme. The ratio of dye molecules to enzyme molecules in the conjugate is not critical, but preferably is as high as possible in order that the emission signal be as intense as possible. The coupling of enzymes and dyes, including affinity labeling, is well-known in the art and further details in this respect are not necessary for a complete understanding of the invention.

The dye-enzyme conjugate is immobilized on a solid support introduced into the body fluid in such a way that the enzyme contacts glucose in the fluid. Excitation light is applied to the dye and fluorescence emission is detected therefrom. Any support material may be used which substantially does not interact with the fluid or interfere with the oxidation reaction or the fluorescence detection system. Exemplary of such supports are glass and plastics, such as polyethylene, polystyrene, polyvinyl chloride and polytetrafluoroethylene.

A particularly preferred support is an optical fiber which, in addition to providing the support for immobilization of the conjugate, also serves as the means for introduction of excitation light to the dye and conduction of fluorescence emission from the dye. Optical fibers act as pipelines for passage of light. They are made of a transparent material, such as glass, and are designed in such a way that very little light can leak out through their sidewalls. A thorough discussion of optical fibers is given by D. M. Considine et al. in Encyclopedia of Chemistry, Van Nostrand Reinhold, (1984) p 645.

The dye-enzyme conjugate may be coated onto a segment of an optical fiber to be contacted with the body fluid. Alternatively, the conjugate may be coated onto a solid support as described above, and the optical fiber brought into intimate contact with the conjugate on the support in such a way that light passed through the fiber is absorbed by the dye. Fluorescence emission from the dye passes back through the fiber and its intensity is measured on a detector.

As mentioned above, fluorescence intensity from the test dye is directly proportional to glucose concentration in the fluid. In order to determine whether the intensity of the emission from the test dye indicates an elevated glucose level in the fluid, a base line level of fluorescence emission may be determined, preferably simultaneously, from the control dye. A second optical fiber may be coated with dye only, the quantity of dye being substantially the same as conjugated to the enzyme. Passage of excitation light through this second optical fiber excites the dye to emit fluorescence which is independent of glucose concentration and thus a measure of ambient oxygen concentration. If the intensity of the emission from the test dye is greater than that from the control dye, an elevated glucose level in the fluid is indicated.

In a preferred embodiment of the method of the invention, the base line level of fluorescence emission from the control dye may be obtained with a second dye-enzyme conjugate. The second conjugate may be prepared in the same way as the first conjugate, except inactive glucose oxidase is used. The enzyme may be rendered inactive, i.e., incapable of catalyzing oxidation of glucose, either prior to or subsequent to coupling to the dye. Methods to inactivate enzymes are routine, well-known to those skilled in the art, and do not constitute a part of this invention.

Most preferably, the inactive enzyme-dye conjugate may be prepared by coating active enzyme-dye conjugate with a membrane. In this embodiment of the method of the invention, active enzyme-dye conjugate immobilized on a first fiber is coated with a selective membrane permeable to molecules the size of glucose and smaller. When introduced into the body fluid, this membrane allows glucose to pass through and contact the conjugate where it is oxidized. Dye in this conjugate is thus the test dye and fluorescence emission therefrom measures glucose concentration. Conjugate on a second fiber is coated with a selective membrane permeable only to molecules the size of oxygen and smaller. Since glucose molecules are larger than oxygen molecules, glucose in the body fluid cannot reach this conjugate to be oxidized, so that its enzyme has, in effect, been inactivated. Oxygen, however, can reach the conjugate and thus provide measurement of ambient oxygen concentration. The dye in this conjugate is thus the control dye, and comparison of the intensities of fluorescence emission from the two dyes indicates, as described above, whether the fluid contains an elevated glucose level.

The method of the present invention may be adapted to quantitate the glucose concentration in a body fluid. In this embodiment of the invention, the intensity of fluorescence emission from the test dye is determined and compared to the intensity of emission determined when the method of the invention is applied to a body fluid having a predetermined glucose concentration. For this embodiment, the invention contemplates a standard curve which relates fluorescence emission intensity, as determined with the device of the invention, to glucose concentration. In accordance with this embodiment of the method, glucose concentration, for example in a diabetic's blood stream, may be ascertained merely by finding the test dye fluorescence intensity on the standard curve and reading the corresponding glucose concentration.

Having now described the method of the invention, various embodiments of the blood glucose monitoring apparatus of the invention will be described with the aid of the figures. FIG. 1 shows glucose monitor 10 having optical fibers 12 and 14, each having a sidewall portion 16 and 17, respectively, and a bottom portion 18 and 19, respectively. Bottom portion 18 of optical fiber 12 has a coating of conjugate 20 of active glucose oxidase conjugated to fluorescent dye (the test dye). Bottom portion 18 of optical fiber 14 has a coating of conjugate 21 of inactive glucose oxidase conjugated to fluorescent dye (the control dye). Alternatively, reference numeral 21, representing the control dye, may be unconjugated fluorescent dye, i.e., the enzyme is omitted. Arrows 22 diagrammatically illustrate excitation light passing down fibers 12 and 14 from a light source (not shown) where it is absorbed by the dyes and emitted therefrom as fluorescence emission 24. Emission 24 returns up fibers 12 and 14 and is measured by a detector (not shown).

FIG. 2 is a vertical sectional view of the apparatus of FIG. 1 after insertion into body fluid 26, illustrated in the Figure as a blood stream. Optical fibers 12 and 14 are shown surrounded by cladding material 27, which separates the fibers and prevents leakage of light through the sidewall portions 16 and 17. Any cladding material conventional in optical fiber technology, such as plastic or glass having a refractive index lower than that of the light-transmissive core of the fiber, may be used.

Figure 3:
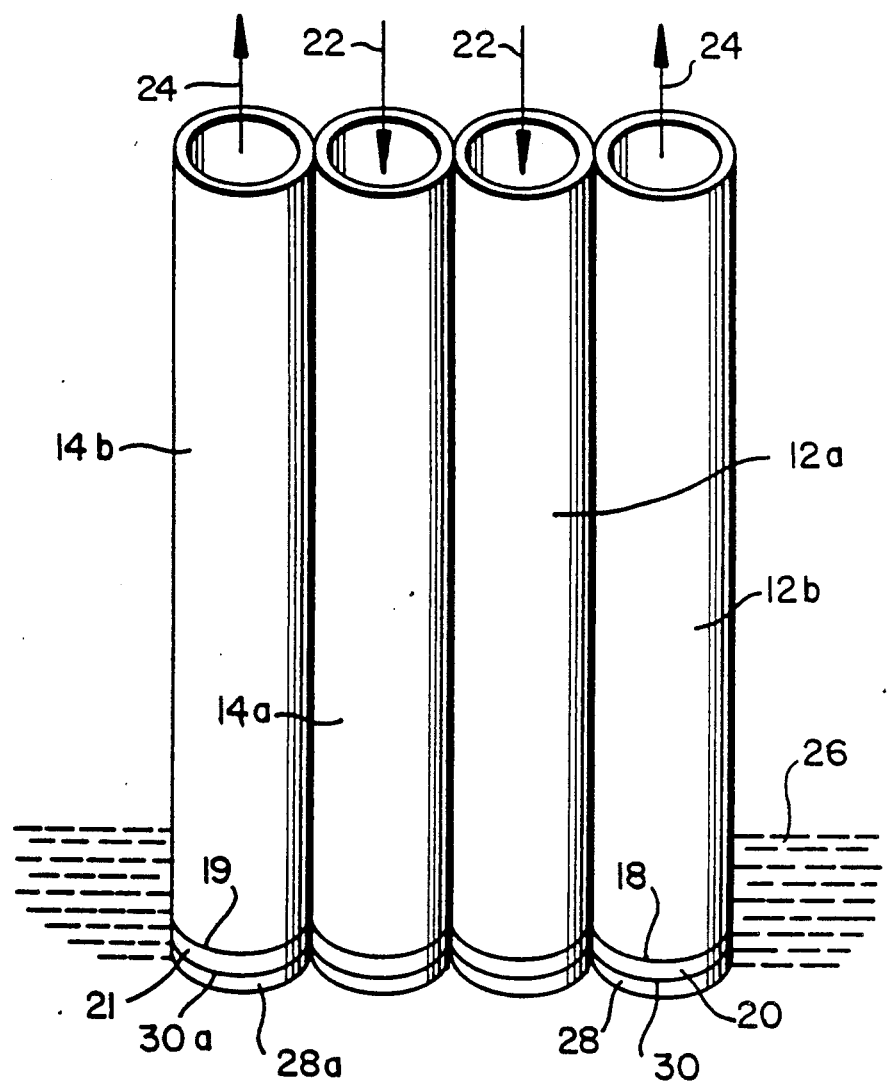
FIG. 3 is a perspective view of an apparatus of the invention using four optical fibers.

An embodiment of the apparatus in which two fibers are used for each of the test dyes and the control dye is shown in FIG. 3. In FIGS. 3–6, elements identical to elements described in FIGS. 1 and 2 are given the same reference numbers and elements similar are given the same base reference number followed by a different suffix (letter).

In FIG. 3, a solid support, shown in the form of a disc 28, is coated on its upper surface 30 with active glucose oxidase-fluorescent dye conjugate 20. Disc 28a is coated on its upper surface 30a with inactive glucose oxidase-fluorescent dye conjugate 21. Discs 28 and 28a preferably are made of a porous plastic material such as polystyrene foam through which the body fluid may freely pass. Optical fibers 12a,12b,14a and 14b are attached to discs 28 and 28a so that their bottom portions 18 and 19 are in intimate contact with conjugate coatings 20 and 21, respectively. Excitation light 22 from the light source passes down fibers 12a and 14a and contacts conjugates 20 and 21 in contact with body fluid 26 in porous discs 28 and 28a where it is absorbed by the fluorescent dye and emitted as fluorescence emission 24. Emission 24 passes up through fibers 12b and 14b to the detector (not shown).

Figure 4:
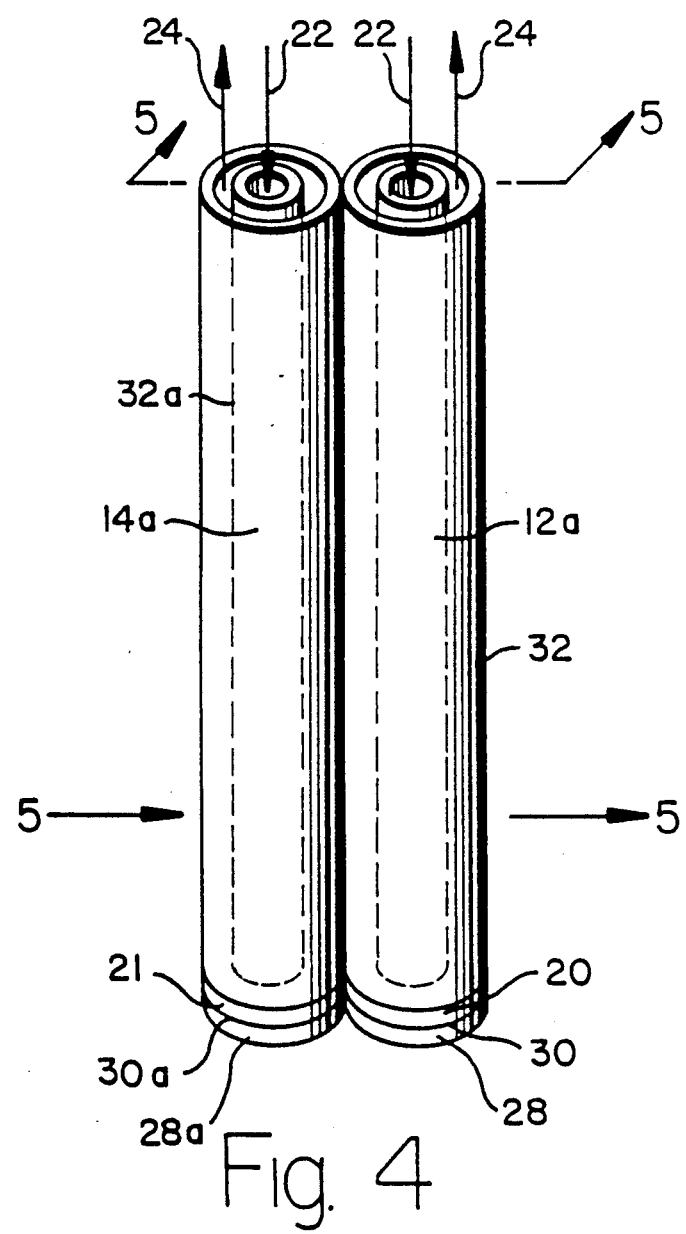
FIG. 4 is a perspective view of an apparatus of the invention using concentric optical fibers.
Figure 5:
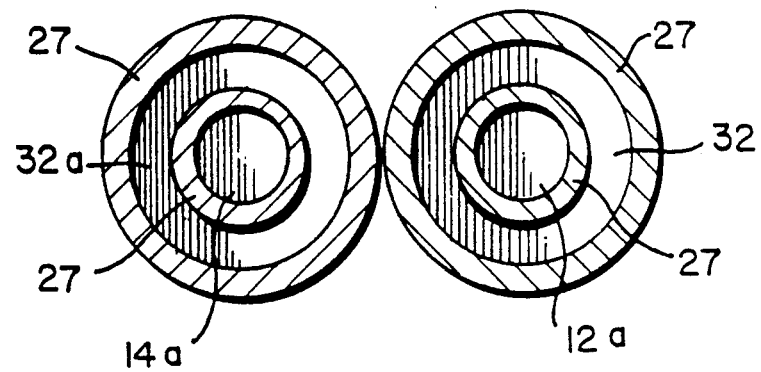
FIG. 5 is a horizontal section view of the apparatus of FIG. 4 taken along line 5—5 thereof.

FIG. 4 gives a perspective view of an embodiment of the apparatus using concentric fibers. Active enzyme-dye conjugate 20 and inactive enzyme-dye conjugate 21 are coated onto upper surfaces 30 and 30a of porous solid supports 28 and 28a, respectively. Optical fibers 12a and 14a have dimensions which allow them to fit inside of hollow optical fibers 32 and 2a. Fibers 12a and 14a and 32 and 32a are separated by layers of cladding material 27, as shown in horizontal sectional FIG. 5.

Figure 6:
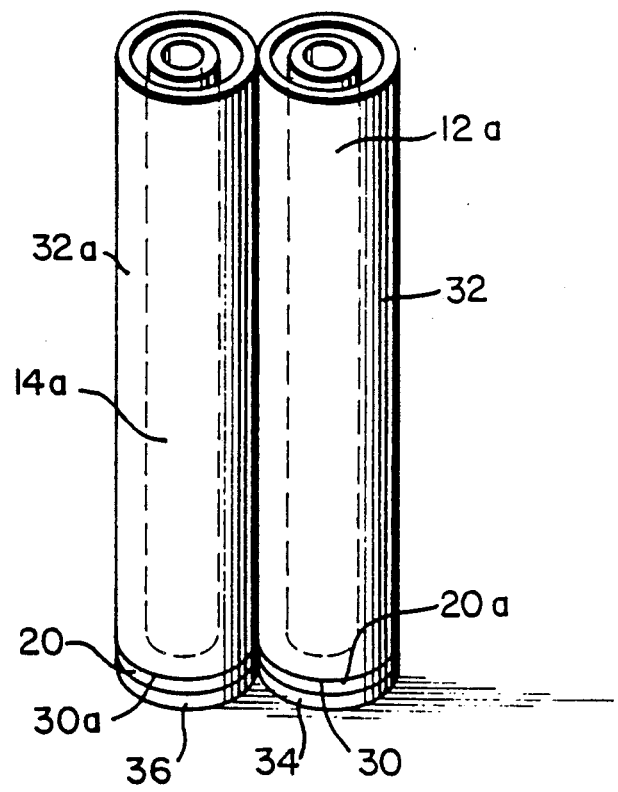
FIG. 6 is a perspective view of an apparatus of the invention, similar to the apparatus of FIG. 4, using enzyme conjugates coated with membranes.

FIG. 6 shows an embodiment of the apparatus in which the conjugates are coated with membranes. Concentric optical fibers 12a and 32 are coated on their bottom surfaces 30 with active enzyme-dye conjugate 20. The coating of conjugate 20a is then itself coated with membrane 34 which is permeable to glucose and molecules smaller than glucose so that its dye serves as the test dye. Concentric optical fibers 14a and 32a are likewise coated on their bottom surfaces 30a with active conjugate 20, which is further coated with membrane 36 permeable only to molecules the size of oxygen and smaller so that its dye serves as the control dye.

It is understood that support discs 28 and 28a, depicted in FIG. 4, may be included in the apparatuses of FIGS. 1 or 6. Likewise, membranes 34 and 36 of FIG. 6 may be included in any of the other embodiments described. The invention is contemplated to encompass these and any other modifications of the apparatus, which provide glucose monitoring in accordance with the principles of the method of the invention herein described.

The following examples are provided to further describe the invention, but are in no way to be considered as limitative.

In summary, the invention provides a system including a method and an apparatus for monitoring of glucose in a body fluid, preferably on a continuous basis. The method is based on oxidation of glucose by glucose oxidase, the extent of oxidation being proportional to glucose concentration. The oxidation reaction depletes oxygen at the active site of the enzyme, and the reduced oxygen concentration is detected and measured by changes in fluorescence intensity proportional to the oxygen concentration. The system may be used either in vitro or in vivo and is particularly suitable for blood glucose determinations. When used in vivo for monitoring glucose concentration in a diabetic's blood stream, the system may be used in conjunction with any insulin delivery system, and is easily adapted for out patient use.

What is claimed is:

1. A method for detecting an elevated glucose level in a body fluid comprising:
   (a) contacting a body fluid containing glucose with a first solid support having immobilized thereon a first conjugate comprising active glucose oxidase and a fluorescent dye, fluorescence emission from said dye being sensitive to oxygen quenching, and with a second solid support having immobilized thereon a second conjugate comprising inactive glucose oxidase and the same aforementioned fluorescent dye whereby said glucose is oxidized by oxygen in said fluid at said first conjugate but not at said second conjugate;
   (b) applying excitation light to said first and second conjugates;
   (c) detecting fluorescence emission from said first and second conjugates;
   (d) comparing the intensities of emission from said first and second conjugates; and
   (e) determining that an elevated glucose level exists in said fluid if said intensity of emission from said first conjugate is greater than said intensity of emission from said second conjugate.

2. The method of claim 1 wherein said body fluid is contacted in vivo in a blood stream of a living being.

3. The method of claim 1 wherein said body fluid is contacted in vitro, said body fluid being selected from the group of fluids consisting of blood and urine.

4. The method of claim 1 wherein said fluorescent dye is selected from the group of dyes consisting of perylen dibutyrate and fluoranthrene.

5. The method of claim 1 wherein said dye is covalently conjugated to said active and said inactive glucose oxidase.

6. The method of claim 4 further comprising a linking group between said dye and said glucose oxidase.

7. The method of claim 1 wherein said first and second solid supports are optical fibers.

8. A method for detecting an elevated glucose level in a body fluid comprising:
   (a) contacting a body fluid containing glucose with first, second, third and fourth optical fibers, said first and second fibers having immobilized thereon a first covalent conjugate of glucose oxidase and a fluorescent dye, fluorescence emission from said dye being subject to oxygen quenching, said first conjugate being coated with a membrane selectively permeable to molecules the size of glucose and smaller, said third and fourth optical fibers having immobilized thereon a second covalent conjugate of glucose oxidase and the same aforementioned fluorescent dye, said second conjugate being coated with a membrane selectively permeable to oxygen but impermeable to glucose, whereby said glucose is oxidized by oxygen in said fluid at said first conjugate ,but not at said second conjugate;
   (b) applying excitation light to said first conjugate through said first fiber and to said second conjugate through said third fiber;
   (c) detecting fluorescence emission from said first conjugate through said second fiber and from said second conjugate through said fourth fiber;
   (d) comparing the intensity of emission from said first conjugate with the intensity of emission from said second conjugate; and
   (e) determining that an elevated glucose level exists in said fluid if said intensity of emission from said first conjugate is greater than said intensity of emission from said second conjugate.

9. A method for quantitating an elevated concentration of glucose in a body fluid comprising:
   (a) contacting a body fluid containing glucose with a covalent conjugate comprising immobilized active glucose oxidase and a fluorescent dye, fluorescence emission from said dye being sensitive to oxygen quenching, whereby glucose is oxidized by oxygen in said fluid at said conjugate;

(b) applying excitation light to said conjugate;
(c) measuring fluorescence emission from said conjugate;
(d) quantitating an elevated concentration of glucose in a body fluid by comparing the magnitude of said emission with the magnitude of fluorescence emission measured when a fluid containing a known quantity of glucose is subjected to steps (a) to (c).

* * * * *